United States Patent [19]

Scott

[11] 4,290,755
[45] Sep. 22, 1981

[54] DENTAL POST AND METHOD OF INSTALLING

[76] Inventor: Edward S. Scott, 1818 S. Cincinnati, Tulsa, Okla. 74119

[21] Appl. No.: 17,350

[22] Filed: Mar. 5, 1979

[51] Int. Cl.³ ............................................. A61C 8/00
[52] U.S. Cl. ................................................ 433/173
[58] Field of Search ............... 433/173, 172, 174, 176

[56] References Cited

U.S. PATENT DOCUMENTS

| | | | |
|---|---|---|---|
| 1,140,539 | 5/1915 | Skinner | 433/172 |
| 2,112,007 | 3/1938 | Adams | 433/174 |
| 3,085,334 | 4/1963 | Bischoff et al. | 433/180 |
| 3,656,236 | 4/1972 | Kuver | 433/221 |
| 3,950,850 | 4/1976 | Driskell et al. | 433/176 |

*Primary Examiner*—Robert Peshock
*Attorney, Agent, or Firm*—Head & Johnson

[57] ABSTRACT

A dental post method of installing posts in the roots of spaced apart teeth having non-parallel root canals by first drilling holes in the teeth in alignment with the root canals, placing a dental post in each of the teeth, measuring the angle of the advergents of the dental posts, and installing permanent dental posts having attachment stems offset relative to the anchor stems, the offset stem dental posts being rotated in the teeth so that the axes of the attachment stems are parallel.

5 Claims, 6 Drawing Figures

DENTAL POST AND METHOD OF INSTALLING

BACKGROUND OF THE INVENTION

I. Field of the Invention

This invention refers to means of removably securing dentures in the mouth of a user. The invention is particularly related to a device and method of employing the device whereby dental posts are secured in two or more teeth having non-parallel root canals and means is provided for arranging the dental posts so that the axis of each is parallel to the other thereby insuring improved anchoring of the denture and improved ease of removing and inserting the denture.

II. Description of the Prior Art

It is known in dentistry to use posts which are permanently anchored to natural teeth to support dentures. An article entitled "Fabrication of a Simple Ball-Socket Attachment" by Joseph T. Quinlivan, D.D.S. in the August, 1974 issue of the Journal of Prosthetic Dentistry, Volume 32, No. 2, and a subsequent article entitled "An Attachment for Overlay Dentures" by Dr. Quinlivan in the September, 1974 issue of the same Journal, Volume 32, No. 3, disclosed a method of attaching dentures. U.S. Pat. No. 2,112,007, issued Mar. 22, 1938 to P. B. Adams for "Anchoring Means for False Teeth" shows a type of ball and socket device. The same general type of device is shown in U.S. Pat. No. 3,085,334 issued Apr. 16, 1963 to J. L. Bischoff et al for a denture attachment. Reference may be also had to U.S. Pat. No. 3,656,236 showing a similar ball-type attachment means.

In addition, Applicant has filed United States Patent application Ser. No. 889,723 on Mar. 24, 1978 entitled "Dental Posts" which disclose improvements in ball and socket type of dental post attachments.

These references disclose the use of a dental post having a segment of a sphere which slips past an o-ring for anchoring dentures but the prior art fails to attack the problem of anchoring dentures in the mouth when posts are anchored in teeth and the posts are not parallel to each other. When a dental post is set in a tooth the first step is to bore a hole in the tooth. This hole must generally follow the root canal of the tooth otherwise there is danger that the hole can penetrate through the side of the tooth, or, the hole can severely weaken the tooth. Natural teeth grow in the mouth in various angles and when two or more spaced-apart natural teeth are employed for anchoring a denture, it is rare that the root canals of the teeth are parallel to each other. This means that manufactured or pre-cast dental posts of the type presently employed, when mounted in holes drilled in natural teeth generally extend in non-parallel relationship. When dentures are inserted in position the recesses in the dentures which receives the posts must accomodate those diverging, non-parallel posts which makes the dentures more difficult to insert and remove, and in addition, impairs the desired objective of a firm, secure fit of the dentures on the dental posts. Prior art requires the fabrication of individual, customized dental posts utilizing the lost wax technique to cast posts that will be parallel when the roots are divergent or convergent, or the optional method of soldering that portion of the posts which extends beyond the root in parallel relationship.

SUMMARY OF THE INVENTION

A method and apparatus of installing dental posts in spaced-apart teeth to receive dentures is provided. The method employs dental posts of the type having a body with an integral anchor stem which is symmetrical in all cross-sections taken perpendicular to the stem axis. In addition the dental post includes an integral attachment stem extending from the body in the direction opposite the anchor stem. In the prior art the axis of the attachment and anchor stem are coincident. The present invention contemplates an apparatus in which the axis of the attachment stem is offset at a preselected angle relative to the axis of the anchor stem. In the practice of the method it is desirable to have available a plurality of dental posts wherein the angle of divergents of the axis of the anchor and the attachment stem are different. In practicing the method a hole is drilled in first and second teeth, each hole being in general alignment with the root canal of the tooth. Attachment posts of the type wherein the anchor stem and the attachment stem portions are coaxial are positioned in the holes drilled in the teeth. The angle of divergents of the axis of the two dental posts is measured, this angle being generally the angle of divergents of the root canals of the two teeth. The user then selects two dental posts wherein the total of the angle of divergents of the dental posts is equal to the measured angle of divergents of the holes drilled in the root canals. These dental posts are then positioned in the drilled holes and rotated so that the two dental posts have their attachment stems extending parallel to each other. The dental posts are then permanently anchored in the holes in the teeth utilizing this orientation.

BRIEF DESCRIPTION OF THE VIEWS

Figure 3:
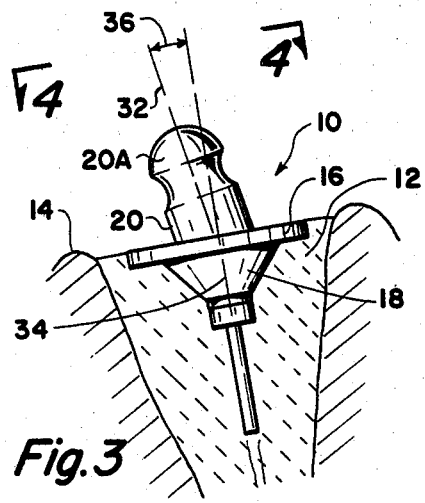

FIG. 3 is a cross-sectional view of a dental post according to the present invention positioned in the hole drilled in the tooth, the dental post having the axis of the attachment stem portion offset relative to the axis of the anchor stem portion so that by employing the method of this invention the dental post can be arranged in the mouth of the user in a manner to insure that the axes of two or more separate dental posts are parallel.

Figure 4:
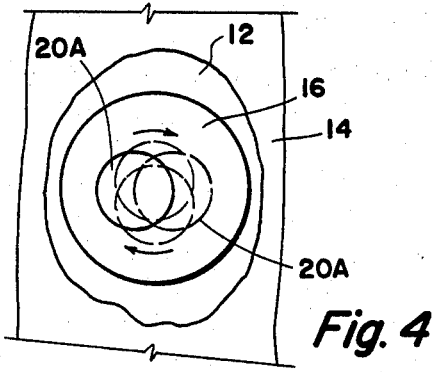

FIG. 4 is a plan view taken along the line 4—4 of FIG. 3 showing how the dental posts of the type shown in FIG. 3 may be rotated to orient the axis of inclination of the attachment stem portion relative to the anchor stem portion to enable two separate dental posts to be arranged to that the attachment stem axes are parallel.

Figure 5:
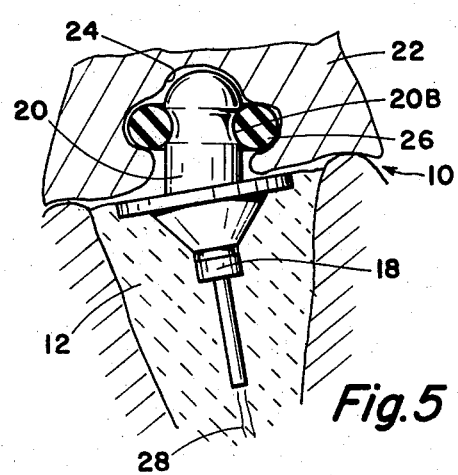

FIG. 5 is a partial cross-sectional view taken through a tooth employing a dental post of this type having an offset attachment stem portion and showing a portion of a denture having an o-ring in recess for receiving the attachment stem portion of the dental post.

Figure 6:
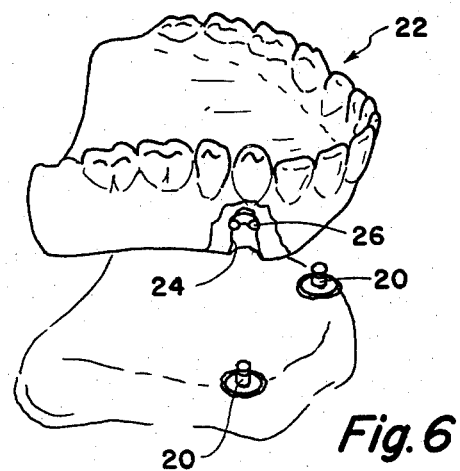

FIG. 6 is an isometric view of the portion of the alveolar ridge of the mouth of a user showing two dental posts mounted in teeth and showing a denture positioned to be received by the dental posts, the denture being partially cut away to show the o-ring in the recess therein.

DESCRIPTION OF THE PREFERRED EMBODIMENT

Figure 2:
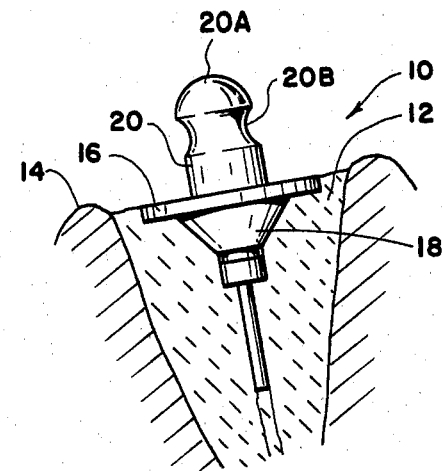
FIG. 2 is a cross-sectional view which shows a dental post positioned in the tooth having been drilled as in FIG. 1, the dental post employed being of the type wherein the axis of the anchor stem and attachment stem portions are coincident so that when anchor posts are positioned in two teeth as in FIG. 6, the angle of divergents of the teeth can be measured.

As previously stated, the use of dental posts implanted in the root portion of natural teeth are frequently employed in anchoring dentures in the mouth of a user. FIG. 2 shows a dental post generally indicated by the numeral 10 mounted in a tooth 12, the tooth having been severed at the gum line 14. The dental post 10 includes a body 16 having an anchor stem portion 18 integrally extending from the body and, extending in the opposite direction, an attachment stem portion 20. The anchor stem 18 may be of a variety of configurations but should be circular about all cross sections taken perpendicular to its axis. The attachment stem 20 has a semispherical top portion 20A and below that, a groove 20B. When the dental post 10 is permanently affixed to tooth 12 a denture, such as indicated by the numeral 22 in FIG. 6, is anchored in place utilizing the dental post. As shown in FIG. 6, the typical denture 20 includes, as illustrated in the cut-away portion, a recess 24 which receives an o-ring 26. The denture 22 is held in place when the o-ring 26 is forced past the semispherical head 20A and into the groove 20B of the attachment stem.

The attachment post 25 shown in FIG. 2 is the type disclosed in the prior art in which the axis of the attachment stem portion 20 is coincident with the axis of the anchor stem portion 18.

Figure 1:
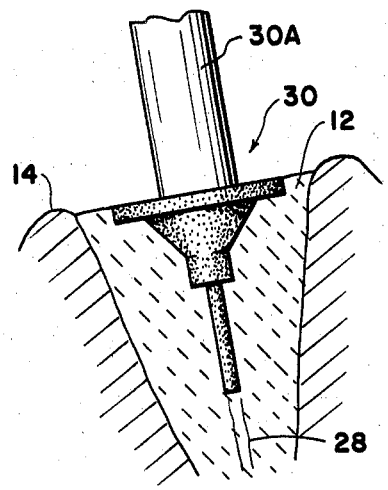
FIG. 1 is a cross-sectional view showing the step of drilling a hole in a tooth which has been cut off to receive a dental post, drill generally following the root canal of the tooth.

The method of installing the dental posts of FIG. 3 is illustrated in FIG. 1. Every natural tooth 12 has a root canal 28. A drill, generally indicated by numeral 30, is utilized having the external configuration of the body 16 and anchor stem 18 of a dental post. The drill 30 has a drill stem 30A which fits into a device (not shown) for rotating the drill. The drill is typically formed of metal and has an abrasive coating on the exterior surface. The drill 30 generally follows the root canal 28. This is true since the root canal represents a small passageway in the tooth which is filled only with soft material. The drill automatically tends to follow the path of least resistance. In addition, the root canal is normally located centrally in the tooth so that by following the root canal the drill tends to remain centrally positioned in the tooth with the maximum tooth material extending to all sides of the hole formed in the tooth by the drill. If the operator trys to substantially depart from the direction of the root canal 28 in the use of drill 30 there is a great chance the tooth will be weakened and the further possibility that the drill can extend through the side of the tooth. For these reasons it can be seen that in the normal course of installing dental posts 10 a hole is drilled following the root canal. The importance of this fact is that teeth are not normally oriented such that the root canals are parallel to each other. Thus, an operator using a drill 30 as in FIG. 1 drilling holes to receive dental posts 10 to support a denture will normally find that when the dental posts are installed into spaced-apart teeth, the axis of the attachment stem 20 of one post is not parallel to the axis of the other post. Thus, when it is required to install two or more dental posts 10 to support dentures in the mouth of the user it is ordinarily found that the dental posts are not parallel to each other. This means that when dentures of the type illustrated by the numeral 20 in FIG. 6 are inserted in the mouth of a user there is difficulty in placement of the dentures over non-parallel attachment stems and once in position the dentures are not held as securely as they would be if the stems were parallel to each other. The essence of this invention is the provision of a dental post and a method of installing it to insure that the attachment stems of two or more dental posts are parallel to each other.

Referring to FIG. 3, a dental post generally indicated by the numeral 10 is shown with the anchor stem portion 18 mounted in the tooth 12 and the hole drilled by a drill bit as shown in FIG. 1 but in which the axis 32 of the attachment stem portion 20 is displaced from the axis 34 of the anchor stem portion 18. The angle of divergents of the axes 32 and 34 of the attachment stem and anchor stem portions of the dental posts as indicated by the numeral 36. In the practice of the method the dentist has available a number of dental posts 10 having different angles 36. Typically, the dental posts may be manufactured wherein the angle of divergents 36 is 5°, 10°, 15°, 20°, 25°, etc. It can be seen that sets of dental posts can be produced having degrees of difference of very small amounts such as differing only by 1° increments. The smaller the degree of increments available to the dentist the more perfectly parallel two or more dental posts can be installed in the mouth of the user.

When the dental posts of FIG. 3 is inserted in a hole formed in the tooth 12 and before it is anchored in position, the dental post may be rotated through a full 360° as shown in FIG. 4 so that when two or more dental posts are employed they may be rotated so as to be parallel to each other in the mouth of the user.

The method of utilizing the dental posts of the type illustrated in FIG. 3 is as follows. The dentist first drills a hole in each of the teeth to be utilized in anchoring a denture. Assuming that the denture is to be anchored with two teeth as illustrated in FIG. 6, the dentist first drills a hole in each of the teeth using a bit as shown in FIG. 1, the bit generally following the root canal of each tooth. After a hole is drilled in each of the two teeth, the dental posts of the type shown in FIG. 2 are inserted in the holes. The post of FIG. 2 is of the type wherein the axis of the anchor stem 18 and the attachment stem 20 are coincident, that is where the angle of divergence is zero. With the zero divergent dental posts in position in the two teeth the dentist then measures the angle of the divergent of the attachment stem portions. Assuming the angle of divergents of the of the attachment stems is 20°, the dentist then removes the dental posts having zero divergents and selects two dental posts having a degree of divergents such that the total equals 20°. For instance, the dentist may select two posts as illustrated in FIG. 3 wherein the angle of the divergents 36 of each is 10° or he may select one post where the angle of divergents is 15° and another where the angle of divergents is 5°. The dentist then inserts the two selected posts into the opening drilled in the two teeth. The posts may then be rotated, as illustrated in FIG. 4, to the position wherein the attachment stems of the two posts are parallel. This establishes the orientation of the dental posts. The dentist may then permanently anchor a post in position such as by noting the orientation, removing the post, depositing a bonding cement in the hole and replacing the dental posts in the selected orientation. In this manner then the dentist has acheived an arrangement wherein the dental posts are permanently secured in the mouth of the user with the axes of the attachment stem portions being parallel to each other.

FIG. 5 is a cross-sectional view of a cut-away portion of a tooth 12 having a dental post 10 therein and having attached to it a denture 22. The denture recess 24 receives the o-ring 26 which fits in the groove 20B of the dental post's attachment stem portion 20. When the attachment stem portions of two or more dental posts are aligned so that the axis of each is generally parallel to the other it can be seen that removing and inserting the denture is much more easily accomplished and, in addition, the denture is more securely anchored in position. If the anchor stem portions are non-parallel the o-rings 26 must be compressed much more in the process of inserting or removing dentures resulting in o-rings being more easily dislodged or quickly worn. Thus the method and apparatus of this invention provides a greatly improved way of providing positive anchoring of removable dentures.

While the invention has been described with a certain degree of particularity it is manifest that many changes may be made in the details and construction of the device and the arrangement for practicing the method of the invention. It is understood that the invention is not limited to the embodiments and the sequence of steps set forth herein, but is to be limited only by the scope of the attached claim or claims, including the full range of equivalency to which each element or step thereof is entitled.

What is claimed is:

1. A dental post for removably securing a denture to the root of a tooth having a root canal, the tooth having a hole drilled therein following the root canal, the denture apparatus having therein a recess defined in part by an elastomeric member having an opening therethrough, the dental post comprising:
    a body having an intermediate enlarged diameter circular portion and having an integral first symmetrical stem circular in all cross sectioned taken perpendicular the stem axis, the first stem being dimensioned for permanent attachment in a drilled hole formed in the root of a tooth; and
    a second integral stem portion extending from said body in the direction opposite said first stem, the second stem having an enlarged outer head portion dimensioned to be received through a denture apparatus elastomeric member by compression of the elastomeric member whereby the elastomeric member applies retentative force to the head portion, and wherein the axis of said second stem is offset by a preselected angle from the axis of said first stem.

2. A dental post according to claim 1 wherein said second stem head portion has a groove on the exterior surface providing a fluid passageway when the head member passes through the opening in the elastomeric member.

3. A dental post according to claim 1 wherein the head member is configured substantially as a segment of a sphere.

4. A method of installing a first and second dental post in the roots of spaced-apart first and second teeth having non-parallel roots, the posts being of the type having a body with an integral symmetrical anchor stem circular in all cross sections taken perpendicular the stem axis and a integral attachment stem extending from the body in the direction opposite the anchor stem, wherein the axis of the attachment stem of at least one of the dental posts is offset from the axis of the anchor stem comprising:
    (a) drilling a hole in each of the first and second teeth, each hole being in general alignment with the root of the tooth;
    (b) placing the anchor stem portion of a dental post in the hole drilled in the first tooth;
    (c) placing the anchor stem portion of a dental post in the hole drilled in the second tooth;
    (d) rotating the dental post having the offset attachment stem portion until the axis thereof is parallel with the axis of the other dental post attachment stem portion.

5. A method of installing a first and second dental post in the roots of spaced-apart first and second teeth having non-parallel root canals, the posts being of the type having a body with an integral symmetrical anchor stem circular in all cross sections taken perpendicular the stem axis and an integral attachment stem extending from the body in the direction opposite the anchor stem and wherein the axis of the attachment stem is offset at a preselected angle from the axis of the anchor stem, the method comprising:
    (a) drilling a hole in each of the first and second teeth, each hole being in general alignment with the root canal of the tooth;
    (b) placing an anchor stem portion of a dental post in the hole drilled in each tooth, the attachment stem of each of both dental posts being coaxial with the anchor stems;
    (c) measuring the angle of divergence of the axes of the attachment stems;
    (d) selecting different dental posts having the attachment stems axes offset from the anchor stem axes so that the combined angle of offset of the two dental posts equal the angle of divergence measured in step (c);
    (e) removing the dental posts inserted in the teeth in step (b) for measuring purposes and inserting the dental posts selected in step (d) into the holes in the teeth;
    (f) rotating the dental posts until their axes are parallel; and
    (g) permanently anchoring the dental posts in the teeth in the orientation established in step (f).

* * * * *